(12) United States Patent
Bara

(10) Patent No.: US 6,399,080 B1
(45) Date of Patent: Jun. 4, 2002

(54) FLOUROUS ANHYDROUS COMPOSITION AND COSMETIC PRODUCTS FOR MAKEUP OR CARE CONTAINING IT

(75) Inventor: Isabelle Bara, Paris (FR)

(73) Assignee: Archimex, Vannes Cedex (FR)

( * ) Notice: Subject to any disclaimer, the term of this patent is extended or adjusted under 35 U.S.C. 154(b) by 0 days.

(21) Appl. No.: 09/291,047

(22) Filed: Apr. 14, 1999

(30) Foreign Application Priority Data

Apr. 15, 1998 (FR) ............................................ 98 04683
Jun. 30, 1998 (FR) ............................................ 98 08339

(51) Int. Cl.$^7$ .............................. A61K 6/00; A61K 7/00
(52) U.S. Cl. ....................................... 424/401; 424/400
(58) Field of Search ................................ 424/400, 401; 568/18

(56) References Cited

U.S. PATENT DOCUMENTS

| | | | | |
|---|---|---|---|---|
| 5,733,526 A | * | 3/1998 | Trevino et al. | 424/9.52 |
| 5,851,539 A | * | 12/1998 | Mellul et al. | 424/401 |
| 6,002,038 A | | 12/1999 | Philippe et al. | |
| 6,030,934 A | * | 2/2000 | Owens et al. | 510/411 |

FOREIGN PATENT DOCUMENTS

| WO | WO 93/11103 | 6/1993 |
|---|---|---|
| WO | WO 94/21233 | 9/1994 |

OTHER PUBLICATIONS

Chemical Abstracts, XP–002091055, AN 126:108664, & JP 08295260 Nov. 12, 1996.

Masamichi Morita et al., "Interfacial Properties and Emulsification in Systems of Perfluoropolyether/Non–Fluorinated Oil/Partially Fluorinated Oligomeric and Polymeric Compounds", Colloids and Surfaces A: Physicochemical and Engineering Aspects, vol. 109, pp. 183–194, 1996.

* cited by examiner

*Primary Examiner*—Dameron L. Jones
(74) *Attorney, Agent, or Firm*—Merchant & Gould PC

(57) ABSTRACT

Homogeneous anhydrous composition comprising in combination at least one fluorous oil and at least one fluorous wax having a carbonaceous skeleton.

This composition finds an application in the preparation of makeup or care products.

13 Claims, No Drawings

FLOUROUS ANHYDROUS COMPOSITION AND COSMETIC PRODUCTS FOR MAKEUP OR CARE CONTAINING IT

This invention has as its subject a homogeneous anhydrous composition comprising in combination at least one fluorous oil and at least one fluorous wax having a carbonaceous skeleton.

This invention also has as its subject makeup or care products containing such anhydrous composition.

The use of fluorous oils in the formulation of cosmetic compositions is sought particularly to the extent that the fluorous oils impart good filmogenic properties and resistance to water and sebum.

Such compositions nonetheless are difficult to achieve, because of the inherent incompatibility of the fluorous oils with numerous polar and apolar hydrocarbonaceous compounds.

Homogeneous combinations of fluorous oils and waxes already have been achieved with the aid of surfactants, but until the present time it has not been possible to obtain in particular fluorous-oil-based anhydrous compositions in the absence of surfactants.

Following numerous studies on various types of compounds, it was found in a surprising and unexpected manner that anhydrous mixtures with complete homogeneity could be achieved by combining certain fluorous oils with at least one fluorous wax having a carbonaceous skeleton.

In addition, it was noted that this particular combination advantageously could constitute the fatty phase of various makeup and care compositions affording in particular an excellent texture and, after application, imparting a considerable softness and a pleasing feel to the skin.

This invention, therefore, has as its subject a homogeneous anhydrous composition or phase comprising in combination at least one fluorous oil and at least one fluorous wax having a carbonaceous skeleton, possibly interrupted by an oxygen atom.

By the term "fluorous wax having a carbonaceous skeleton" is understood a compound solid at room temperature, having a melting point in excess of or equal to approximately 30° C. and containing a number of fluorine atoms preferably in excess of that of the hydrogen atoms, the carbonaceous skeleton possibly being interrupted by at least one oxygen atom. This wax contains only fluorine, hydrogen and carbon, and possibly oxygen, atoms.

By oil is understood a non-aqueous liquid compound, at room temperature (25° C.).

Among the fluorous oils compatible with the fluorous waxes having a carbonaceous skeleton, there may be cited in particular the perfluorous compounds, fluorous silicones, fluoroalkyl and heterofluoroalkyl compounds.

By perfluorous compounds is understood, in accordance with the invention, compounds in which all the hydrogen atoms have been substituted by fluorine atoms.

A—Among the perfluorous compounds corresponding to this definition, there may be cited in particular:

1) the perfluoropolyethers corresponding to the following formulas (I) and (II):

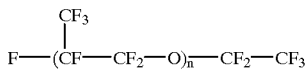

in which:

n is 7 to 30; and

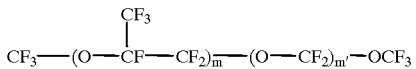

the m/m' ratio being from 20 to 40, and
the molecular weight being from 500 to 20000.

Among these perfluoropolyethers of formulas (I) and (II), there may be cited respectively the one sold under the name of "Fluortress LN36®" by the company DUPONT, and those sold under the general name of "Fomblin" by the company MONTEFLUOS, for example Fomblin HC R® with vapor tension $10^7$ mmHg.

2) the perfluorocycloalkyl compounds of the following formula (III):

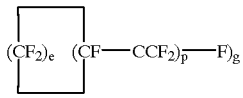

in which:

e is equal to 4 or 5, g is equal to 1 or 2, and p is equal to 1,2 or 3;

on condition that when g=2, the groupings are not necessarily in alpha with respect to each other.

Among the compounds of formula (III), there may be cited in particular perfluoromethylcyclopentane and perfluorodimethylcyclohexane, sold respectively under the names of "Flutec PC1®" with vapor pressure of 368 mbar and "Flutec PC3®" by the company BNFL FLUOROCHEMICALS Ltd.; and 3) the perfluorophenanthrene sold under the name of "Flutec PC11®" by the company BNFL FLUOROCHEMICALS Ltd.

B—Among the fluorous silicones, there may be cited in particular the fluoro-silicone compounds corresponding to the following formula (IV):

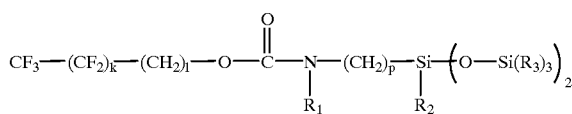

in which:

k is 1 to 17, l is 1 to 18, p is 1 to 6, and $R_1$ represents a hydrogen atom or a $C_1$–$C_6$ alkyl radical, $R_2$ represents a $C_{1-C6}$ alkyl radical or the radical—OSi $(R_3)_3$, and $R_3$ represents a $C_1C_4$ alkyl radical.

Among the compounds corresponding to formula (IV), there may be cited in particular:

N-(-2-F-octyl-ethyloxycarbonyl)-3-aminopropyl bis (trimethylsiloxy)methylsilane, N-(-2-F-hexyl-ethyloxycarbonyl)-3-aminopropyl bis (trimethylsiloxy)methylsilane, N-(-2-F-butyl-ethyloxycarbonyl)-3-aminopropyl bis (trimethylsiloxy)methylsilane, N-(-2-F-octyl-ethyloxycarbonyl)-3-aminopropyl tris (trimethylsiloxy)silane, N-(-2-F-hexyl-ethyloxycarbonyl)-3-aminopropyl tris (trimethylsiloxy)silane, and N-(-2-F-butyl-ethyloxycarbonyl)-3-aminopropyl tris (trimethylsiloxy)silane.

C—Among the fluoroalkyl or heterofluoroalkyl compounds, there may be cited those corresponding to the following formula (V):

in which:

t is equal to 0 or 1, h is equal to 0, 1, 2 or 3, i is equal to 2, 3, 4 or 5, and Z represents O, S or $NR_4$ $R_4$ representing hydrogen, a $-(CH_2)_h-CH_3$ or $-(CF_2)_i-CF_3$ radical.

Among the compounds of formula (V), there may be cited in particular the methoxynonafluorobutane sold under the name of "MSX 4518®" by the company 3M (t=1, Z=O, n=0 and m=3) or the ethoxynonafluorobutane sold under the name of "HFE 7200" by the company 3m (t=1, Z=O, n=1 and m=3).

The oils of the invention have a boiling temperature of <220° C., preferably less than 120° C.

Among the fluorous waxes having a carbonaceous skeleton, as defined above, capable of forming a homogeneous anhydrous composition with the fluorous oils, there may be cited in particular the fluorous esters corresponding to the following formula (VI):

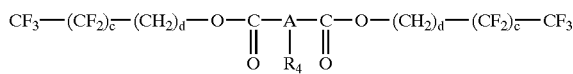

in which:

$R_4$ represents a hydrogen atom or the radical

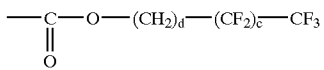

A represents a $C_1-C_{18}$ alkylene or alcenylene chain, straight or branched, possibly hydroxylated, c is 1 to 17, and d is 1 to 18.

Among the compounds of formula (VI), there may be cited in particular the 2F-octyl-ethyl dodecane 1,12, dioate of the following formula:

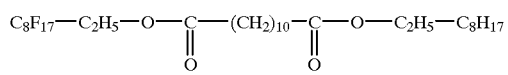

and the $C_1-C_6$ perfluoroalkyl tri-citrates, more particularly the perfluorobutyl tri-citrate sold under the name of "Zonyl TBC®" by the company DUPONT.

As other fluorous waxes usable in the invention, there may be cited the polytetrafluoroethylene (PTFE) waxes.

Waxes having a melting point ranging from 45° C. to 150° C., in particular such as the fluorous esters of formula (VI), preferably are used.

In the anhydrous composition according to the invention, the fluorous oils generally are present in a proportion ranging between 20 and 95% by weight, but preferably between 60 and 80% by weight in relation to the total weight of the composition.

The fluorous waxes having a carbonaceous skeleton generally are present in a proportion ranging between 5 and 80% by weight, but preferably between 20 and 40% by weight in relation to the total weight of the composition.

According to a particular embodiment, the anhydrous composition such as defined above may contain, in addition, one or several other fatty substances which may be chosen from among the oils, waxes, gums and/or so-called pasty fatty substances.

a—The oils of the anhydrous composition may be of mineral, animal, vegetable or synthetic origin, these possibly being volatile or non-volatile at room temperature.

As an oil of mineral origin, there may be cited in particular paraffin oil.

As an oil of animal origin, there may be cited in particular squalene or perhydrosqualene.

As an oil of vegetable origin, there may be cited in particular sweet almond oil, calophyllum oil, palm oil, avocado oil, jojoba oil, sesame oil, olive oil, castor oil and the cereal-germ oils such as, for example, wheat-germ oil.

As a synthetic oil, there may be cited in particular:

(1) the esters of formula:

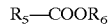

in which:

$R_5$ represents the remnant of a $C_7-C_{20}$ higher fatty acid, and $R_6$ represents a hydrocarbonaceous $C_3-C_{30}$ radical.

Among these esters, there may be cited in particular: Purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, isononyl isononanoate, the esters derived from lanolic acid such as isopropyl lanolate and isocetyl lanolate.

As other synthetic oils, there additionally may be cited isododecane, isohexadecane, the polyisobutenes and hydrogenated polyisobutene, as well as the acetylglycerides, the polyalcohol octanoates and decanoates such as those of glycol and glycerol, the alcohol or polyalcohol ricinoleates such as cetyl ricinoleate, propylene glycol dicaprylate and diisopropyl adipate;

(2) the fatty alcohols such as oleic alcohol, linoleic alcohol, linolenic alcohol, isostearyl alcohol and octyldodecanol;

(3) silicone oils such as the possibly functionalized straight polydiorganosiloxanes, the cyclic polydiorganosiloxanes and in particular the cyclotetra- and penta-dimethicones and the organopolysiloxanes such as the alkyl, alcoxy or phenyl dimethicones and in particular phenyltrimethicone;

The oils may represent from 0 to 50% and better still from 0 to 20% of the total weight of the composition.

b—The waxes of the anhydrous composition, other than the fluorous waxes, may be of mineral, fossil, animal, vegetable or synthetic origin or even be hydrogenated oils or fatty acids solid at 25° C.

Among the mineral waxes, there may be cited in particular the microcrystalline waxes, paraffin, vaseline and ceresin.

Among the fossil waxes, there may be cited ozokerite and montan wax.

Among the waxes of animal origin, there may be cited beeswax, spermaceti, lanolin wax, as well as the derivatives originating from lanolin such as the lanolin alcohols, hydrogenated lanolin, hydroxylated lanolin, acetylated lanolin, lanolin fatty acids and acetylated lanolin alcohol.

Among the waxes of vegetable origin, there may b cited in particular candelilla wax, carnauba wax, Japan wax and cocoa butter.

Among the synthetic waxes, there may be cited in particular the homopolymers of ethylene and the copolymers of ethylene and a monomer corresponding to the following formula:

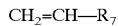

in which:
  $R_7$ represents a $C_{1-C30}$ radical, an aryl or aralkyl radical; $R_7$ preferably being a methyl, ethyl, propyl, isopropyl, butyl, decyl dodecyl or octadecyl radical.

Waxes obtained by Fisher-Tropsch synthesis as well as silicone waxes also may be used.

Among the hydrogenated oils solid at 25° C., there may be cited in particular hydrogenated castor oil, hydrogenated palm oil, hydrogenated tallow and hydrogenated coconut oil.

Among the fatty esters solid at 25° C., there may be cited in particular propylene glycol mono-myristate and myristyl myristate.

As waxes usable in the compositions in accordance with the invention, there additionally may be cited cetyl alcohol, stearyl alcohol, the mono-, di- and triglycerides solid at 25° C., stearic monoethanolamide, colophane and its derivatives as well as the glycol and glycerol abietates, the sucroglycerides and the calcium, magnesium, zinc and aluminum oleates, myristates, lanolates, stearates and dihydroxystearates.

Waxes having a melting point ranging from 45° C. to 150° C. preferably are used. They represent in particular from 0 to 20% of the total weight of the composition.

c—The fatty substances of the pasty type may be of mineral, animal, vegetable or synthetic origin.

Among the pasty fatty substances, there may be cited in particular the synthetic esters such as arachidyl propionate, vinyl polylaurate, the polyethylene waxes and the organopolysiloxanes such as the alkyldimethicones, the alcoxydimethicones or the dimethicone esters.

This invention also has as its subject a composition or a product for makeup or care containing a homogeneous anhydrous composition or phase such as defined above.

According to a first particular embodiment, the makeup or care product is anhydrous and contains the homogeneous anhydrous composition in a proportion ranging between approximately 0.5 and 100% by weight in relation to the total weight of the product.

This anhydrous product may be offered in the form of a stick such as, for example, a lipstick or a stick for under-eye circles, or in the form of an anhydrous compact such as, for example, a makeup foundation, an eye shadow, a blush or a mascara.

When the anhydrous product is in the form of a stick or a compact, this may contain pigments as well as fillers in the form of fine particles having an average size ranging between 0.02 and 50 μm.

The pigments may be mineral or organic or even in the form of metallic lakes. Among these pigments, there may be cited titanium dioxide, zinc oxide, D&C Red No. 36 and D&C orange No. 17, the calcium lakes of D&C Red No. 7, 11, 31 and 34, the barium lake of D&C Red No. 12, the D&C Red No. 13 strontium lake, the aluminum lakes of FD&C Yellow No. 5, FD&C Yellow No. 6, D&C Red No. 27, D&C Red No. 21, FD&C Blue No. 1, the iron oxides, manganese violet, chromium oxide and ultramarine blue.

The fillers may be of natural or synthetic origin. Among these, there may be cited in particular:
  i) mineral powders such as talc, kaolin, mica, silica, the silicates, alumina, the zeolites, hydroxyapatite, sericite, the micatitaniums, barium sulfate, bismuth oxychloride, boron nitride and metallic powders such as aluminum powder;
  ii) vegetable powders such as starch, corn, wheat or rice powders;
  iii) organic powders such as Nylon, polyamide, polyester, polytetrafluoroethylene or polyethylene powders.

Furthermore, these various powders may be coated, for example, with metallic salts of fatty acids, amino acids, lecithin, collagen, silicone compounds, fluorous compounds or with any other customary coating.

In addition to the pigments such as defined above, at least one coloring agent also may be present and, among these, there may be cited the derivatives of eosin such as D&C Red No. 21 and the derivatives of halogenated fluorescein such as D&C Red No. 27, D&C orange No. 5 in combination with D&C Red No. 21 and D&C orange No. 10.

In the makeup or care products, the proportion of pigment(s) and/or coloring agent(s) generally ranges between approximately 0.1 and 25% and better still between 0.1 and 15% by weight in relation to the total weight of these products.

The fillers generally may be present in the makeup or care products in a maximum proportion of approximately 98% by weight in relation to the total weight of these products.

The anhydrous products such as defined above also, of course, may contain one or several conventional cosmetic or dermatological additives or adjuvants.

According to a second embodiment, the makeup or care product is a dispersion, in the form of a stable water-in-oil (W/O) or oil-in-water (O/W) emulsion, which consists essentially (i) of a homogeneous anhydrous composition or phase such as defined above in a proportion ranging between approximately 0.1 and 50% by weight in relation to the total weight of the composition, (ii) of an aqueous phase in a proportion ranging between approximately 4 and 97% by weight in relation to the total weight of the composition, and (iii) of at least one emulsifying agent in a proportion ranging between approximately 0.5 and 10% by weight in relation to the total weight of the dispersion.

As an emulsifying or surfactant agent which may be used in the compositions in the form of a W/O or O/W emulsion, there may be cited in particular those belonging to the family of dimethicone copolyols and the alkyl- or alcoxydimethicone copolyols. Among the latter, there may be cited in particular the compounds corresponding to the following general formula:

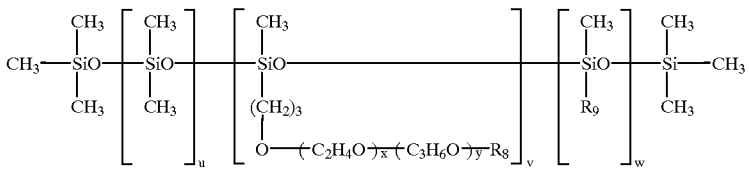

in which:

$R_8$ is a hydrogen atom, a $C_1$-$C_{16}$ alkyl, an alcoxy or acyl, $R_9$ is a $C_8$-$C_{45}$ alkyl or alcoxy radical, u=0 to 200, v=1 to 40, w=0 to 100, the molecular weight of the radical —O—$(C_2H_4O)_x$—$(C_3H_6O)_y$—$R_8$ being from 250 to 2000, x and y being chosen in such manner that the ratio by weight of the oxyethylene/oxyproplyene groups ranges between 100:0 and 20:80.

Among the commercial products which may contain all or a portion of the alkyldimethicone copolyols, there may be cited in particular those sold under the name of "Abil WE09®," "Abil EM90®" or Abil WS08®" by the company GOLDSCHMIDT; "Q2 5200®" or "Q2 3225C®" by the company DOW CORNING and "218 1138®" by the company GENERAL ELECTRIC.

The surfactant agents also may be chosen from among the anionic or non-ionic surfactant agents. On this subject, one may refer to the document "Encyclopedia of Chemical Technology, KIRK-OTHMER," volume 22, pages 333–432, 3rd edition, 1979 WILEY, for the definition of the properties and the functions (emulsifying) of surfactants, in particular pages 347–377 of this reference, for anionic and non-ionic surfactants.

The surfactants of these two groups preferably used in the compositions according to the invention are:

among the non-ionic surfactants: the fatty acids, fatty alcohols, the polyethoxylated or polyglycerol fatty alcohols, such as polyethoxylated stearyl or cetylstearyl alcohol, the esters of fatty acids and saccharose, the alkyl glucose esters, in particular the polyoxyethylene fatty esters of alkyl($C_1$–$C_6$)glucose, and among the anionic surfactants: the amine stearates.

These dispersions are offered preferably in the form of creams and may be used as makeup or care products.

The products or compositions such as described above, whether of the anhydrous type or in the form of a dispersion, afford excellent cosmetic properties such as, in particular, an excellent texture, as well as a very good staying quality on the skin as regards rubbing, water or sebum.

These products or compositions such as they have just been described above may contain, in addition, one or several conventional cosmetic adjuvants such as vitamins; hormones; antioxidant agents; preservatives; fragrances; thickeners; hydrating agents; moisturizing agents; anionic, non-ionic or amphoteric polymers; active cosmetic or dermatological ingredients.

The invention is illustrated by the following examples, wherein the quantities are expressed in weight.

EXAMPLES OF COSMETIC COMPOSITION

Example 1

Lipstick

According to the invention, a lipstick is prepared by undertaking mixture of the following ingredients:

Polyperfluoroisopropylether sold under the name of "Fluortress LM 36®" by the company DUPONT . . . 5 g 2F-octyl-ethyl dodecane 1,12 dioate . . . 40 g Perfluorodecaline . . . 35 g Methoxynonafluorobutane sold under the name of MS X 4518®" by the company 3M . . . 10 g Pigments . . . 10 g Example 2

Makeup Foundation in Stick Form

According to the invention, a makeup foundation is prepared by undertaking mixture of the following ingredients:

2F-octyl-ethyl dodecane 1,12 dioate . . . 30 g

N-(-2-F-octyl-ethyloxycarbonyl)-3-amino-propyl bis (trimethylsiloxy)methylsilane . . . 60 g Pigments . . . 10 g Example 3

Care Cream

A water-in-oil emulsion is prepared with the following ingredients according to the standard methods for manufacture of emulsions:

FLUORTRESS LM 36 (1) . . . 10 g

Zonyl TBC (2) . . . 8 g

Tri-fluoromethyl $C_{1-4}$ alkyl dimethicone (Shin Etsu) . . . 12 g

Abil WE 09 (3) . . . 5 g

Salt . . . 0.7 g

Water . . . qsp 100 g (1) poiyperfluoroisopropyl ether (Dupont de Nemours)

(2) tri-perfluoroalkyl ethyl citrate (Dupont de Nemours)

(3) polyglyceryl-4 isostearate/cetyldimethicone copolyol/hexyl laurate (Goldschmidt).

What is claimed is:

1. Homogeneous anhydrous composition, comprising in combination at least one fluorous oil and at least one fluorous wax having a carbonaceous skeleton, wherein said fluorous oil is selected from the group consisting of:

$$CH_3—(CH_2)_h—[Z]_t—(CF_2)_i—CF_3 \qquad (V)$$

in which:

t is equal to 0 or 1, h is equal to 0, 1, 2, or 3, i is equal to 2, 3, 4, or 5, and Z represents O, S or $NR_4$ $R_4$ represents hydrogen, a —$(CH_2)_h$—$CH_3$ or —$(CF_2)_i$—$CF_3$ radical, and in which the fluorous wax having a carbonaceous structure is of the following formula (VI):

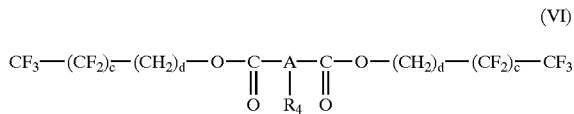

(VI)

in which:

R$_4$ represents a hydrogen atom or the radical

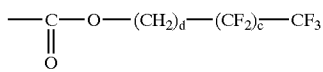

A represents a C$_1$–C$_{18}$ alkylene or alkenylene chain, straight or branched, optionally hydroxylated, c is 1 to 17, and d is 1 to 18.

2. Composition according to claim 1, wherein the fluorous wax having a carbonaceous skeleton is selected the group consisting of 2F-octyl-ethyl-dodecane 1,12 dioate, trifluoroalkyl ethyl citrate and perfluorobutyl tri-citrate.

3. Composition according to claim 1, wherein the fluorous oil is present in a proportion ranging between 20 and 95% by weight in relation to the total weight of the composition.

4. Composition according to claim 1, characterized by the fact that the fluorous wax having a carbonaceous skeleton is present in a proportion ranging between 5 and 80% by weight in relation to the total weight of the composition.

5. Makeup or care product containing at least one homogeneous anhydrous composition, according to claim 1.

6. Product according to claim 5, wherein said composition is present in a proportion ranging between 0.5 and 100% by weight in relation to the total weight of the product.

7. Product according to claim 5, characterized by the fact that it is employed for the preparation of an anhydrous product in the form of a stick or compact.

8. Product according to claim 5, wherein the product is employed for the preparation of a product in the form of a dispersion or emulsion of the water-in-oil or oil-in-water type and contains said composition in a proportion ranging between 0.1 and 50% by weight, an aqueous phase present in a proportion ranging between 4 and 97%, and an emulsifying agent.

9. Product according to claim 5, wherein it contains at least one pigment and/or a coloring agent in a proportion ranging between 0.1 and 15% by weight in relation to the total weight of the product.

10. Product according to claim 5, wherein it contains, in addition, a filler present in a maximum proportion of 98% by weight in relation to the total weight of the product.

11. Product according to claim 5, wherein it contains active cosmetic or dermatological ingredients.

12. Homogeneous anhydrous composition, comprising in combination at least one fluorous oil having the formula (V):

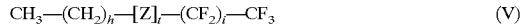

(V)

in which:

t is equal to 0 or 1, h is equal to 0, 1, 2, or 3, i is equal to 2, 3, 4, or 5, and Z represents O, S or NR$_4$ R$_4$ represents hydrogen, a —(CH$_2$)$_h$—CH$_3$ or —(CF$_2$)$_i$—CF$_3$ radical, and at least one fluorous wax having a carbonaceous skeleton, wherein said fluorous was having a carbonaceous structure is selected from the group consisting of fluorous esters corresponding to the following formula (VI):

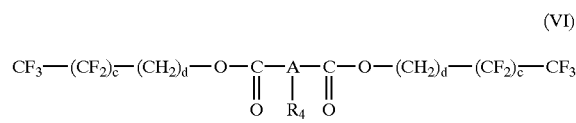

(VI)

in which:

R$_4$ represents a hydrogen atom or the radical

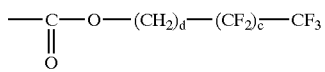

A represents a C$_1$–C$_{18}$ alkylene or alkenylene chain, straight or branched, optionally hydroxylated, c is 1 to 17, and d is 1 to 18.

13. Composition according to claim 12, wherein the fluorous wax having a carbonaceous structure is selected from the group consisting of N-(-2-F-octyl-ethyloxycarbonyl)-3-aminopropyl bis (trimethylsiloxy)methylsilane, N-(-2-F-hexyl-ethyloxycarbonyl)-3-aminopropyl bis (trimethylsiloxy)methylsilane, N-(-2-F-butyl-ethyloxycarbonyl)-3-aminopropyl bis (trimethylsiloxy)methylsilane, N-(-2-F-octyl-ethyloxycarbonyl)-3-aminopropyl tris (trimethylsiloxy)silane, N-(-2-F-hexyl-ethoxycarbonyl)-3-aminopropyl tris (trimethylsiloxy)silane, and N-(-2-F-butyl-ethyloxycarbonyl)-3-aminopropyl tris (trimethylsiloxy)silane.

* * * * *